US009115984B2

(12) United States Patent
Lee et al.

(10) Patent No.: US 9,115,984 B2
(45) Date of Patent: Aug. 25, 2015

(54) METHOD OF GENERATING HEIGHT INFORMATION IN CIRCUIT BOARD INSPECTION APPARATUS

(75) Inventors: Seung-Hyun Lee, Daegu (KR); Hyun-Ki Lee, Daegu (KR); Min-Young Kim, Daegu (KR); Jea-Hong Lee, Ulsan (KR)

(73) Assignees: KOH YOUNG TECHNOLOGY INC., Seoul (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 14/347,137

(22) PCT Filed: Dec. 28, 2011

(86) PCT No.: PCT/KR2011/010243
§ 371 (c)(1),
(2), (4) Date: Mar. 25, 2014

(87) PCT Pub. No.: WO2013/100223
PCT Pub. Date: Jul. 4, 2013

(65) Prior Publication Data
US 2014/0219542 A1 Aug. 7, 2014

(30) Foreign Application Priority Data
Dec. 27, 2011 (KR) .................. 10-2011-0143531

(51) Int. Cl.
*G06K 9/62* (2006.01)
*G06T 7/00* (2006.01)
(Continued)

(52) U.S. Cl.
CPC ............ *G01B 11/0608* (2013.01); *G01B 11/24* (2013.01); *G01N 21/956* (2013.01);
(Continued)

(58) Field of Classification Search
CPC ... G06T 7/0004; G06T 7/0042; G01N 21/956
See application file for complete search history.

(56) References Cited

U.S. PATENT DOCUMENTS 5,416,562 A * 5/1995 Ota et al. ..................... 355/53
7,545,512 B2 * 6/2009 Kim et al. .................... 356/514
(Continued)

FOREIGN PATENT DOCUMENTS

JP 2004-226128 8/2004
JP 2008-14940 1/2008
(Continued)

OTHER PUBLICATIONS

International Search Report for International Application No. PCT/KR2011/010243 dated Dec. 14, 2012.
(Continued)

*Primary Examiner* — Samir Ahmed
(74) *Attorney, Agent, or Firm* — Kile Park Reed & Houtteman PLLC (57) ABSTRACT

A method of generating height information in a circuit board inspection apparatus, first, obtaining a first image corresponding to a first area and a second image corresponding to a second area with partially overlapped to the first area of a test board. Next, the first image and the second image are matched based on the overlapped area of the first and second area. Sequentially, a relative positional relationship of the first and second images is obtained from the result of matching. Sequentially, a combined grid image is generated by combining the first grid image and the second grid image based on the relative positioning relationship, wherein the first and second grid images are obtained by irradiating a grid patterned light toward a measurement object formed on the board inspection apparatus. Therefore, it is possible to generate an exact height information.

15 Claims, 8 Drawing Sheets

(51) Int. Cl.
 H05K 13/08 (2006.01)
 G01B 11/24 (2006.01)
 G01N 21/956 (2006.01)
 G01B 11/06 (2006.01)
 G01N 21/88 (2006.01)

(52) U.S. Cl.
 CPC ............ G06T7/0004 (2013.01); G06T 7/0042 (2013.01); H05K 13/08 (2013.01); *G01N 21/8806* (2013.01); *G01N 2021/95638* (2013.01); *G06T 2207/10004* (2013.01); *G06T 2207/30141* (2013.01)

(56) References Cited

U.S. PATENT DOCUMENTS

| | | | | |
|---|---|---|---|---|
| 2003/0062487 | A1* | 4/2003 | Hiroi et al. | 250/492.2 |
| 2005/0002554 | A1* | 1/2005 | Schulze et al. | 382/144 |
| 2005/0116187 | A1* | 6/2005 | Uda et al. | 250/559.45 |
| 2009/0207426 | A1* | 8/2009 | Zandifar | 358/1.9 |
| 2010/0165116 | A1* | 7/2010 | Hsieh et al. | 348/187 |
| 2010/0302364 | A1* | 12/2010 | Kim et al. | 348/136 |
| 2011/0002529 | A1* | 1/2011 | Jeong et al. | 382/147 |

FOREIGN PATENT DOCUMENTS

| | | |
|---|---|---|
| JP | 2008-191122 | 8/2008 |
| JP | 2010-169433 | 8/2010 |
| JP | 2011-10300 | 1/2011 |
| KR | 10-1056995 | 8/2011 |
| KR | 10-1059697 | 8/2011 |
| WO | 2011/087337 | 7/2011 |

OTHER PUBLICATIONS

Written Opinion of the International Searching Authority for International Application No. PCT/KR2011/010243, dated Dec. 14, 2012.

* cited by examiner

Figure 9

METHOD OF GENERATING HEIGHT INFORMATION IN CIRCUIT BOARD INSPECTION APPARATUS

TECHNICAL FIELD

Exemplary embodiments of the present invention relate to a method of generating height information in a circuit board inspection apparatus. More particularly, exemplary embodiments of the present invention relate to a method of generating height information in a circuit board inspection apparatus through capturing image with at least two cameras.

BACKGROUND ART

In general, at least one printed circuit board is equipped in an electronic device and circuit pattern, connection pad, driving chip electronically coupled to the connection pad, etc. are mounted on these printed circuit boards.

In general, a circuit board inspection apparatus is used to confirm if various elements as mentioned above are mounted or aligned properly.

In a conventional circuit board inspection apparatus, it is general to use single camera to capture image, but recently, two cameras are used to capture images to improve inspection speed and resolution.

However, in case of dividing a measurement object in two areas and capturing image with two cameras, credibility of measurement result may fall when exact combination of the two captured images is failed.

Therefore, it is requested an exact matching technology of captured images when a measurement object is split and at least two cameras are used two capture them.

DISCLOSURE

Technical Problem

Therefore, an object of the present invention is to provide a method of matching exactly captured images when at least two cameras are used to capture images during circuit board inspection so that exact height measurement can be performed with advantages of using at least two cameras.

Technical Solution

According to an exemplary embodiment of the present invention, a method of generating height information in circuit board inspection apparatus comprises, first, capturing and obtaining a first image corresponding to a first area and a second image corresponding to a second area with partially overlapped to the first area of a test board; matching the first image and the second image based on the overlapped area between the first and second area; obtaining a relative positional relationship between the first image and second image using the result of the matching; and generating combined height information by combining a first grid image corresponding to the first area and a second grid image corresponding to the second area, wherein the first and second grid images are captured by using grid patterned light to the measurement object formed on a circuit board based on the relative positional relationship.

For example, a plurality of dots may be marked on the test board. An identifier may be formed on the test board, and the identifier is comprised within the overlapped area.

In an exemplary embodiment, the method of matching the first and second images based on the overlapped area between the first and the second area may further comprise selecting a feature dots among the marked dots within the overlapped area; and matching a first feature dots presented in the first image and a second dots presented in the second image.

In an exemplary embodiment, the plurality of dots marked on the test board may be aligned in a matrix form, the overlapped area may comprise a matching line that comprises at least a row of the matrix, and the first image and second image may be matched based on the matching line.

In an exemplary embodiment, the method may further comprise, before capturing the first area and the second area with partially overlapped to the first area of a test board, screening remaining dots in the matrix that are included in the matching line so that they are not captured as an image.

The method of matching the first image and the second image based on the overlapped area may comprise generating a predicted image corresponding to the second image connected to the first area by using matrix form of dots shown in the first image of the first area; and matching the predicted image and the second image based on the overlapped area.

Based on the matching result, obtaining a relative positioning relationship between the first and the second image may further comprise obtaining s, m11, m12, m13, m21, m22, m23, m31, m32, and m33 satisfying an equation as follows;

$$s\begin{bmatrix} u1 \\ v1 \\ 1 \end{bmatrix} = \begin{bmatrix} m11 & m12 & m13 \\ m21 & m22 & m23 \\ m31 & m32 & m33 \end{bmatrix} \begin{bmatrix} u2 \\ v2 \\ 1 \end{bmatrix},$$

wherein (u1, v1) is a coordinate of the first area and (u2, v2) is a second coordinate of the second area that are matched at one point within the overlapped area.

The method of matching the first image and the second image based on the overlapped area may be configured to match at least 5 points to obtain the equation as above.

According to another exemplary embodiment of the present invention, a method of generating height information in a circuit board inspection machine comprises, irradiating a measurement object formed on a circuit board with a grid patterned light; capturing and obtaining a first gird image corresponding to a first area and a second grid image corresponding to a second area with partially overlapped to the first area of the measurement object; obtaining a first height information corresponding to the first grid image and a second height information corresponding to the second grid image using bucket algorithm for the first image and the second image; and generating a combined height information by combining the first and second height information that are obtained by using relative positional relationship between the first and second area, wherein the relative positional relationship is obtained by using the overlapped area between the first and second area.

The first height information may comprise a first measured height H1, the second height information may comprise a second measured height H2, and the method of generating combined height information by combining the first and second height information, the first and second height information are obtained by using relative positional relationship between the first and second area, may further comprise matching the first and the second area by using the positional relationship; obtaining a and b that satisfies to equation H1=aH2+b; and generating the combined height information by using the obtained a and b.

According to another exemplary embodiment of the present invention, a method of generating height information comprises irradiating a measurement object formed on a board with a grid patterned light; capturing and obtaining a first grid image corresponding to a first area and a second grid image corresponding to a second area with partially overlapped to the first area of the measurement object; generating a combined grid image using a relative positioning relationship between the first and second area, the relative positioning relationship is obtained by using the overlapped area between the first and second area; and obtaining a combined height information corresponding to the combined grid image using bucket algorithm.

The method of generating the combined grid image by combining the first and second grid images and using relative positioning relationship between the first and the second area, wherein the relative positioning relationship is obtained by using the overlapped area between the first and second area, may comprise matching the first and second area by using the positioning relationship; and obtaining b that satisfies to equation H1=H2+b in the overlapped area between the first and second area; and generating the combined grid image by using the obtained b.

The method of generating height information of circuit board inspection apparatus may further comprise calculating a credibility index for the first and second grid images, the credibility index may comprise at least one received signal intensity, modulation, visibility and signal-to-noise ratio of the grid patterned light, one of inferior credibility, of the first area and the second area, may be compensated to the other superior credibility.

Advantageous Effects

According to the present invention above, a relative position relation between images obtained by a plurality of cameras is obtained and images are matched using the obtained position relation so that a precise matching image can be performed.

Thus, it is possible to obtain exact height information with high resolution and high inspection speed which are benefits of multiple camera usage by obtaining final height information from combined grid image or combined height information.

| <Code Description> | |
|---|---|
| 50: test board | 52: dot |
| 100a: first camera | 120a: second camera |
| 130a: beam splitter | 200a: image capturing part |
| AR1: first area | AR2: second area |
| FD: feature dot | ID: identifier |
| OA: overlapped area | |

MODE FOR INVENTION

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to comprise the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

For convenience, same numerals are used for identical or similar elements of an apparatus of cutting a tempered board and the conventional one.

Hereinafter, with reference to the drawings, preferred embodiments of the present invention will be described in detail.

Figure 1:
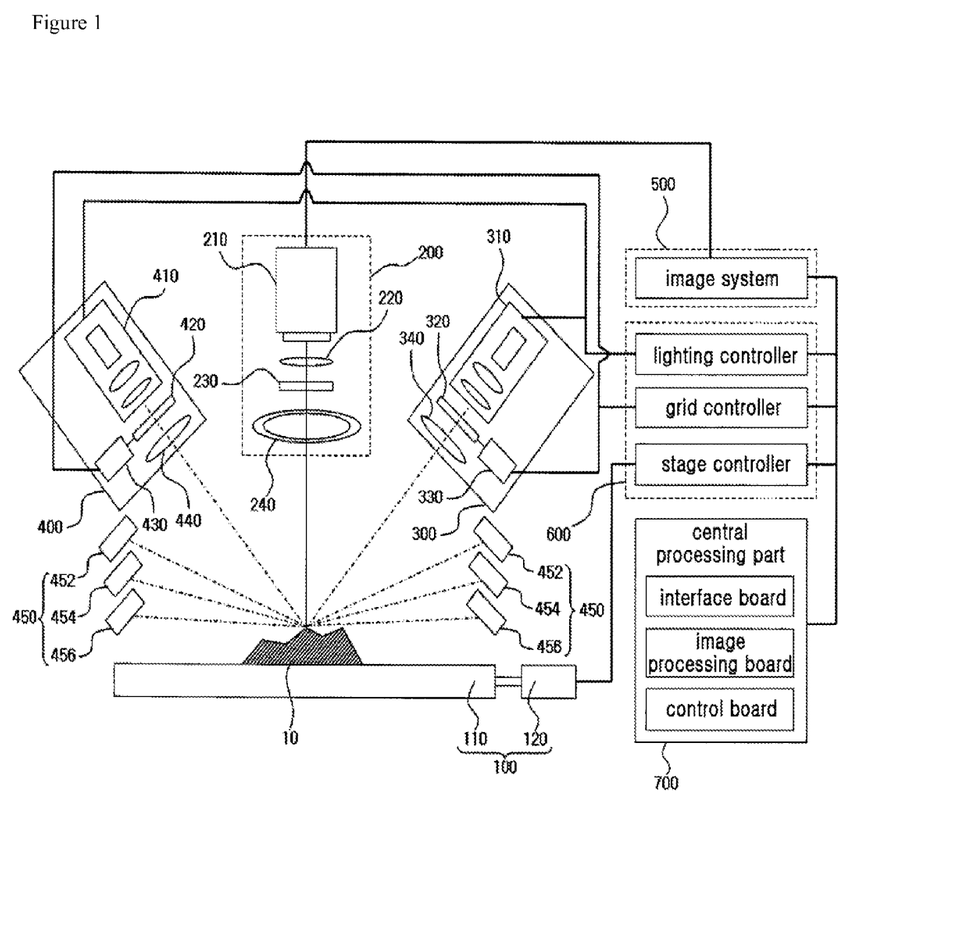
FIG. 1 is a schematic diagram of a circuit board inspection apparatus according to an embodiment of the present invention.

FIG. 1 is a schematic diagram of a circuit board inspection apparatus according to an embodiment of the present invention.

Referring to FIG. 1, a circuit board inspection apparatus according to an embodiment of the present invention may comprise a measurement stage part 100, an image capturing part 200, a first lighting part comprising a first and a second lighting devices 300 and 400, a second lighting part 450, an image obtaining part 500, a module controlling part 600, and a central processing part 700.

The measurement stage part 100 may comprise a stage part 100 supporting a measurement object 10 and a stage transfer unit 120 moving the stage 110. In the present embodiment, a measurement position of measurement object 10 may be changed by moving the measurement object 10 toward the first and the second lighting device 300 and 400 through the stage part.

The image capturing part 200 is disposed above the stage 110 to receive reflective light from the measurement object 10 and capture image of the measurement object 10. In other words, the image capturing part 200 receives light irradiated from the first and second lighting devices 300 and 400 and reflected light from the measurement object 10 to capture planar image of the measurement object 10.

The image capturing part 200 may comprise a camera 210, an imaging lens 220, a filter 230, and a circular lamp 240. The camera captures planar image of the measurement object 10 by receiving the light that is reflected from the measurement object 10, for example, CCD camera or CMOS camera may be adopted. The imaging lens 220 is disposed under the camera to make an image with the reflected light from the measurement object in the camera 210. The filter 230 is disposed under the imaging lens 220 to provide a filtered light, which is reflected from the measurement object 10, to the imaging lens 220, for example, it may be one of frequency filter, color filter and light intensity adjustment filter. The circular lamp 240 is disposed under the filter 230 to provide light to the measurement object 10 to capture unusual image such as two-dimensional shape.

The first lighting device 300 may be disposed, for example, at a right side of the image capturing part and in an inclined with respect to the stage 110 supporting the measurement object 10. The first lighting device 300 may comprise a first lighting unit 310, a first grid unit 320, a first grid transfer unit 330, and a first condensing lens 340. The first lighting unit 310 generates light with at least one lens and a lighting source, and the first grid unit 320 is disposed under the first lighting unit 310 to convert the light from the first lighting unit 210 to a first grid patterned light. The first grid transfer unit 330 is connected to the first grid unit 320 to transport it, and as an example, piezoelectric (PZT) transfer unit or fine linear transfer unit may be adopted. The first imaging lens 340 is disposed under the first grid unit 320 to make an image of the first grid patterned light irradiated by the first grid unit 320 to the measurement object 10.

The second lighting device 400 may be disposed, for example, at a left side of the image capturing part 200 in an inclined manner with respect to the stage 110 supporting the measurement object. The second lighting device 400 may comprise a second lighting unit 410, a second grid unit 420, a second grid transfer unit 430, and a second condensing lens 440. As the second lighting device is substantially same as the first lighting device 300, duplicated description is skipped.

When the first lighting device 300 irradiates the measurement object 10 with a first grid patterned light for N times by moving sequentially N times the first grid unit 320 through the first grid transfer unit 330, the imaging capturing unit 200 may capture N grid first images by receiving sequentially the reflected lights from the measurement object 10. Also, when the second lighting device 400 irradiates the measurement object 10 with a second grid patterned light for N times by moving sequentially N times the second grid unit 420 through the second grid transfer unit 430, the imaging capturing unit 200 may capture N grid second images by receiving sequentially the reflected lights from the measurement object 10. Herein, N is natural number, which, for example, and may be 3 or 4.

Meanwhile, in this embodiment, only the first and second lighting device 300 and 400 that emit the first and second grid patterned lights are explained, but alternatively, there may be more than 3 lighting devices. In other words, grid patterned lights may be emitted in various directions toward the measurement object 10 to capture various types of images.

For example, when three lighting devices are disposed in a form of regular triangle, three grid patterned lights are emitted in 3 different directions toward the measurement object 10, when four lighting devices are disposed in form of square of which center is the image capturing part 200, four grid patterned lights are emitted in 4 different directions toward the measurement object 10. Also, the first lighting device may comprise 8 lighting units, in this case, grid patterned lights are emitted in 8 directions to capture an image.

The second lighting part 450 irradiates the measurement object 10 with light to obtain two-dimensional planar image of the measurement object 10. In an exemplary embodiment, the second lighting part 450 may comprise a red light 452, a green light 454, and a blue light 456. For example, the red light 452, the green light 454, and the blue light 456 are disposed above the measurement object in circular form and may emit each of red light, green light, and blue light toward the measurement object 10, or may be disposed in different height to each other as shown in FIG. 1.

The image obtaining part 500 is electrically coupled to the camera 200 of the image capturing part 200 and stores the obtained patterned images from the first lighting part. Also, the image obtaining part 500 stores the two-dimensional images that are captured from the second lighting part 450. For example, the image obtaining part 500 comprises an image system that receives and stores the N first patterned images and the B second patterned images that are captured from the camera 210.

The module controlling part 600 is electrically coupled to and controls the measurement stage part 100, the image capturing part 200, the first lighting device 300, and the second lighting device 400. For example, the module controlling part 600 comprises a lighting controller, a grid controller, and a stage controller. The lighting controller controls the first and second lighting unit 310 410 and emits lights, the grid controller controls each of the first and second grid transfer units 33 430 and moves the first and second grid units 320 and 420. The stage controller controls the stage transfer unit 120 and moves the stage 110 to vertical and horizontal direction.

The central processing part 700 is electrically coupled to and controls the image obtaining part 500 and the module controlling part 600. Specifically, the central processing part 700 receives the N first images and the N second images from the image system of the image obtaining part 500 and processes them to measure a three-dimensional shape of the measurement object 10. Also, the central processing part 700 may control each of the lighting controller, the grid controller, and the stage controller of the module controlling part 600. In this way, the central processing part 700 may comprise an image processing board, a control board and an interface board.

The image capturing part 200 of the circuit board inspection apparatus as described above may comprise at least two cameras.

Figure 2:
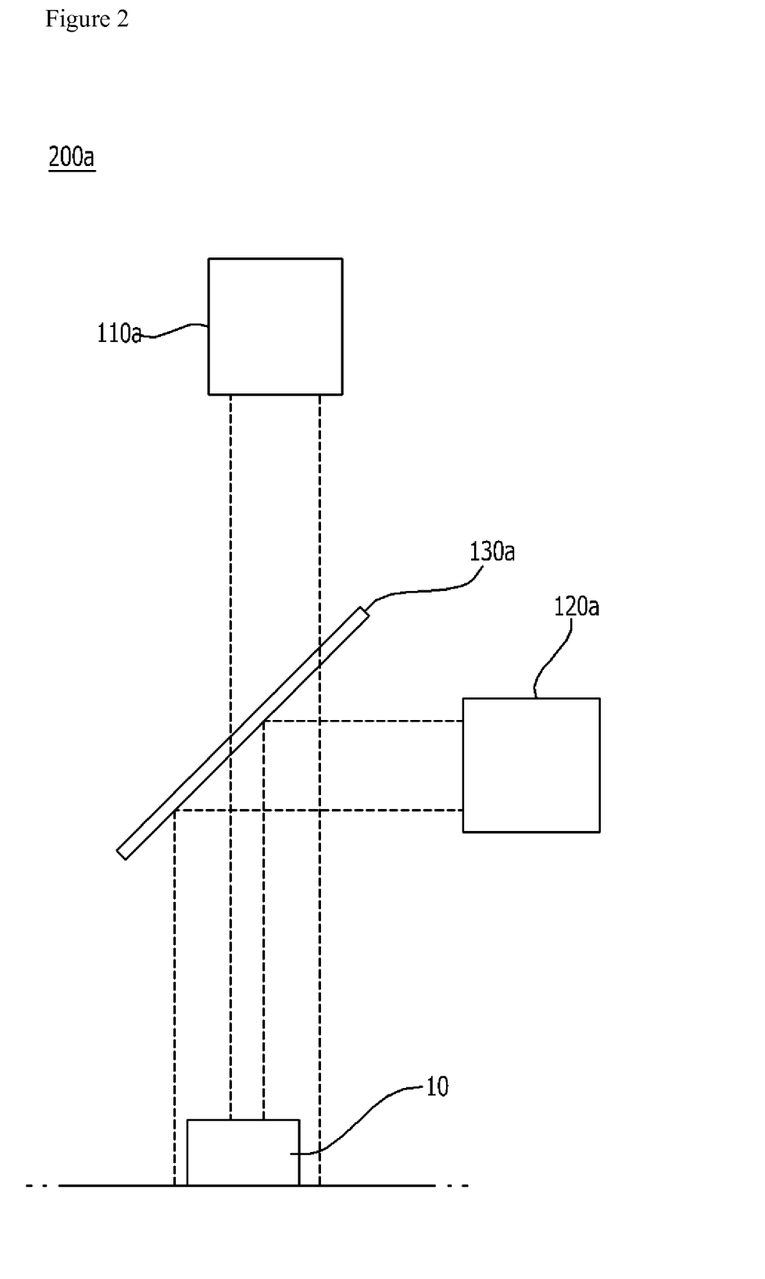
FIG. 2 is a schematic diagram explaining an image capturing part of the circuit board inspection apparatus according to an embodiment of the present invention.

FIG. 2 is a schematic diagram explaining an image capturing part of the circuit board inspection apparatus according to an embodiment of the present invention.

Referring to FIG. 2, an image capturing part 200a of a circuit board inspection apparatus of an exemplary embodiment comprises a first camera 110a, a second camera 120a and a beam splitter 130a to inspect a measurement object. The image capturing part 200a comprises at least two cameras and obtains split images of the measurement object 10.

The first camera 110a obtains at least a portion image of the measurement object 10, and the second camera 120a obtains at least a part image of the measurement object 10

The beam splitter 130a transmits a part and reflects a part of lights that is reflected from the measurement object 10, and transmits them to the first and second cameras 110a and 110b.

An image of the measurement object 10 is obtained by combining the two obtained images as the obtained images from the first and second cameras 110a and 110b are captured from different portion of the measurement object.

Figure 3:
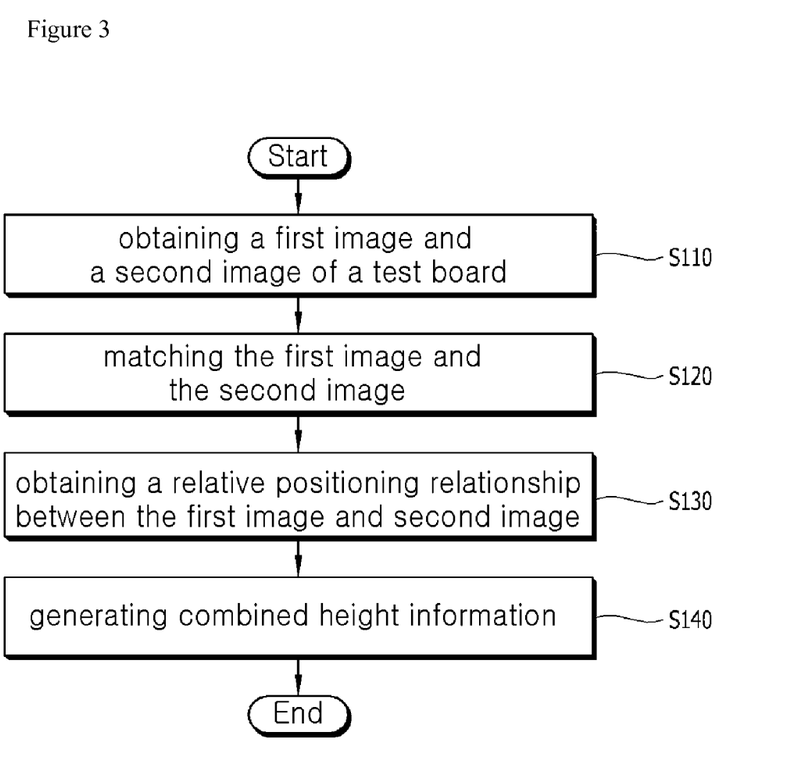
FIG. 3 is a flow chart showing a method of generating height information in a circuit board inspection apparatus according to an embodiment of the present invention.
Figure 4:
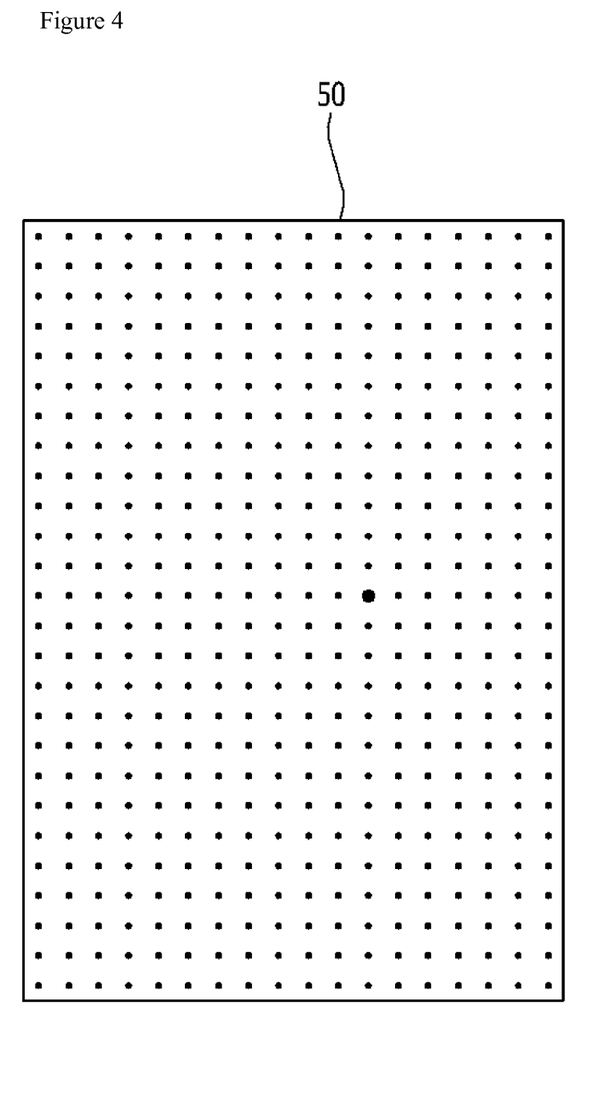
FIG. 4 is a plain view of a test board of FIG. 2 adopted in the circuit board inspection apparatus according to an embodiment of the present invention.
Figure 5:
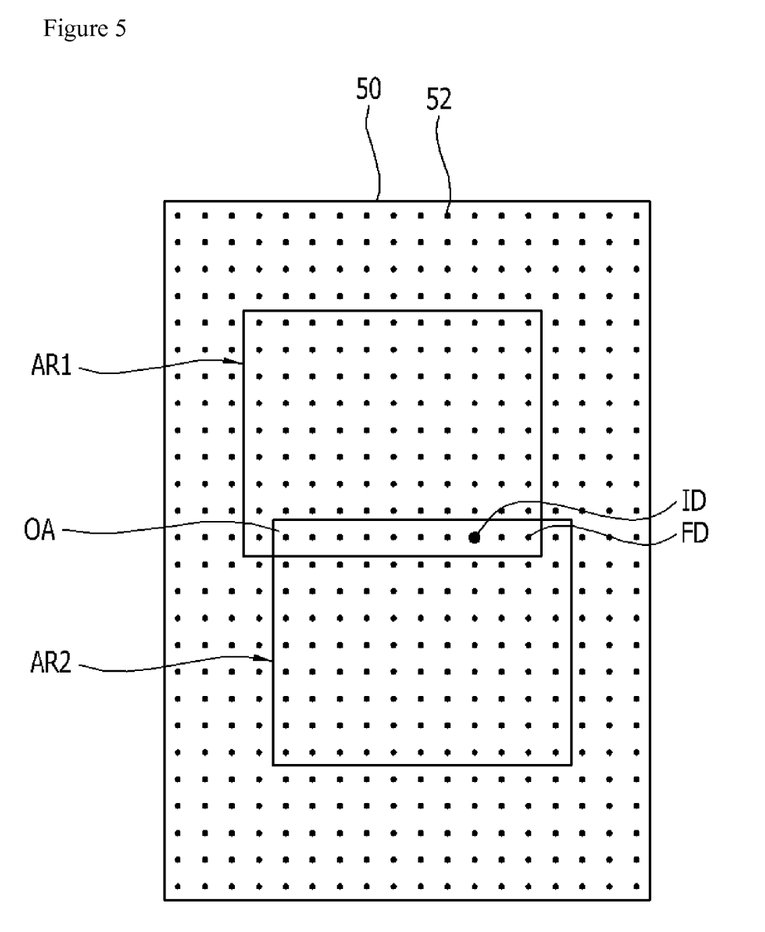
FIG. 5 is a plain view explaining matching method of a first image and a second image for generating height information in the circuit board inspection apparatus of FIG. 3 according to an embodiment.

FIG. 3 is a flow chart showing a method of generating height information of a circuit board inspection apparatus according to an embodiment of the present invention, FIG. 4 is a plain view of a test board of FIG. 1 adopted in the circuit board inspection apparatus according to an embodiment of the present invention, and FIG. 5 is a plain view explaining matching method of a first image and a second image for generating height information in the circuit board inspection apparatus of FIG. 2 according to an embodiment.

Referring to FIGS. 2-5, in order to generate height information in the circuit board inspection apparatus 100, obtaining a first image IM1 of a first area AR1 and a second image IM2 of a second area AR2 with partially overlapped to the first area AR1 of a test board (S110). In other words, two images IM1 and IM2 are obtained by capturing two areas AR1 and AR2 that with partially overlapped to each other of the test board 50.

The test board 50 is an object for processing an adjustment process for establishing a relative positioning relationship between the first and second images IM1 and IM2, and is adopted to obtain the relative positioning relationship before measuring the object.

For example, in the test board 50, a plurality of dots 52 may be marked as shown in FIG. 5. In this case, for example, the plurality of dots 52 marked in the test board 50 may be aligned in matrix form.

An identifier ID may be formed on the test board 50, and the identifier ID is included within the overlapped area OA. The identifier ID may be formed in various form to prevent matching error during matching process of the first and second images IM1 and IM2 based on the overlapped area OA. Accordingly, the identifier may be formed by giving feature to one of the plurality dots, or be formed between the dots. For example, the identifier ID may be formed by enlarging a size of one dot in the overlapped area OA as shown in FIG. 5. Otherwise, the identifier may be a cross sign formed between the dots.

Subsequently, matching the first image IM1 and the second image IM2 based on the overlapped area OA of the first area AR1 and the second area AR2 (S120).

The first area AR1 and the second area AR2 are two divided portion of the upper surface of the test board 50, as the overlapped area OA is common area between the first area AR1 and the second area AR2, a combined image of upper surface of the test board 50 is obtained by matching the first image IM1 of the first area AR1 and the second image IM2 of the second area AR2 based on the overlapped area OA.

As explained above, if the identifier ID is formed in the overlapped area OA, it may be more advantageous to match the first image IM1 and the second image IM2.

According to an exemplary embodiment, matching the first and second images IM1 and IM2 based on the overlapped area OA (S120) may be done as below.

First, selecting feature dots FD among the plurality of dots, the feature dots are used as a reference during the matching process. For example, the feature dots FD may be a portion of a row located on rightmost of the overlapped area OA of the test board 50 as shown in FIG. 5.

Subsequently, matching the feature dots FD shown in the first image IM1 and the feature dots FD shown in the second image IM2. In this case, if the identifier ID is formed in the overlapped area OA as shown in FIG. 5, it may be more advantageous to match the first image IM1 and the second image IM2.

Figure 6:
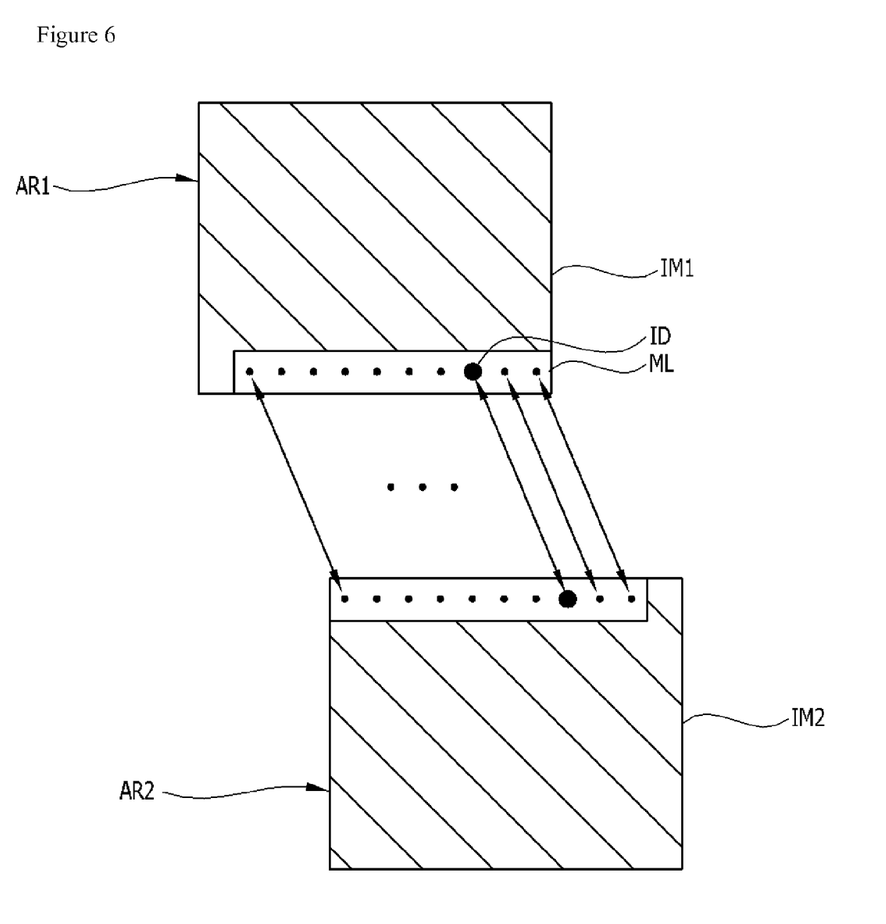
FIG. 6 is a plain view explaining another embodiment of matching method of a first image and a second image for generating height information in the circuit board inspection apparatus of FIG. 3.

FIG. 6 is a plain view explaining another embodiment of matching method of a first image and a second image for generating height information in the circuit board inspection apparatus of FIG. 3.

Referring to FIG. 6, the overlapped area OA may comprise a matching line ML comprising at least one line of the matrix where the plurality of dots are aligned in matrix form in the overlapped area OA. And the first image IM1 and the second image IM2 may be matched based on the matching line ML.

Before capturing the first image IM1 corresponding to the first area AR1 of a test board 50 and the second image IM2 corresponding to the second area AR2 with partially overlapped to the first area AR1 (S110), remaining dots of the matrix that are not included in the matching line may be screened such that they are not captured as an image, and as a result, matching error may be prevented. In FIG. 5, the blocked portion is depicted as oblique lines.

Figure 7:
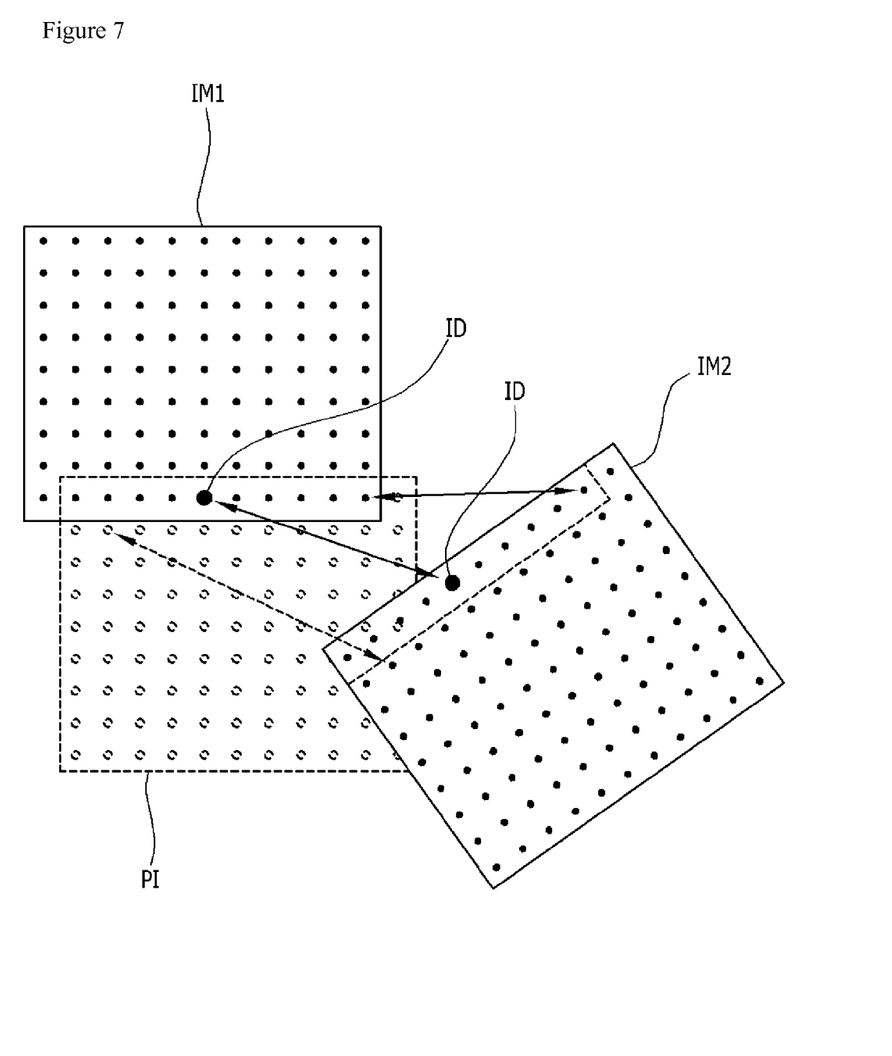
FIG. 7 is a plain view explaining another embodiment of matching method of a first image and a second image for generating height information in the circuit board inspection apparatus of FIG. 3.

FIG. 7 is a plain view explaining another embodiment of matching method of a first image and a second image for generating height information in the circuit board inspection apparatus of FIG. 3.

Referring to FIG. 7, matching the first image and second images IM1 and IM2 based on the overlapped area OA of the first area AR1 and the second area AR2 (S120) may be performed as below.

First, generating a predicted image PI corresponding to the second area AR2 and connecting the first image IM1 using matrix form shown in the first image IM1.

The predicted image PI is a virtual image that is naturally driven from the first image IM1. Accordingly, the predicted image PI corresponds to an expanded image of the first image IM1.

Subsequently, matching the predicted image PI and the second image IM2 based on the overlapped area OA. In this case, the aforementioned identifier ID, the matching line, and the like above may be applied as it is. Arrows shown in FIG. 7 shows an example relationship between the dots.

Referring again to FIG. 3, obtaining a relative positioning relationship of the first image IM1 and the second image IM2 using the matching result (S130).

In this case, the relative position relation can be obtained by an equation as below.

$$s \begin{bmatrix} u1 \\ v1 \\ 1 \end{bmatrix} = \begin{bmatrix} m11 & m12 & m13 \\ m21 & m22 & m23 \\ m31 & m32 & m33 \end{bmatrix} \begin{bmatrix} u2 \\ v2 \\ 1 \end{bmatrix}$$ [Equation 1]

Wherein (u1,v1) is a coordinate of the first area AI1 and (u2,v2) is a second coordinate of the second area AR2 that are matched at one point within the overlapped area OA.

The relative positioning relationship may be defined by obtaining s, m11, m12, m13, m21, m22, m23, m31, m32, and m33 of the matrix of the equation. Wherein, s corresponds to a scale factor.

A point 1 is a point within a two-dimensional plane, so that, with respect to the point 1, an equation for u1, u2 and v2 and another equation for v1, u2 and v2 can be obtained. Also, s may be expressed with u2 and v2.

Accordingly, by matching at least 5 points among the ten unknown numbers s, m11, m12, m13, m21, m22, m23, m31, m32, and m33, the all unknown numbers may be solved.

Subsequently, generating a combined height information by combining a first grid patterned and a second grid patterned based on the positioning relationship (S140). The first and second grid images are captured by irradiating the first area AR1 and the second area AR2 of the measurement object formed on the board inspection apparatus with grid patterned light toward.

In other words, and after obtaining a positioning relationship by using the test board 50 before measuring the measurement object 10, the first and second grid images are combined using the positioning relationship, and a combined height information may be generated using the combined grid image.

Figure 8:
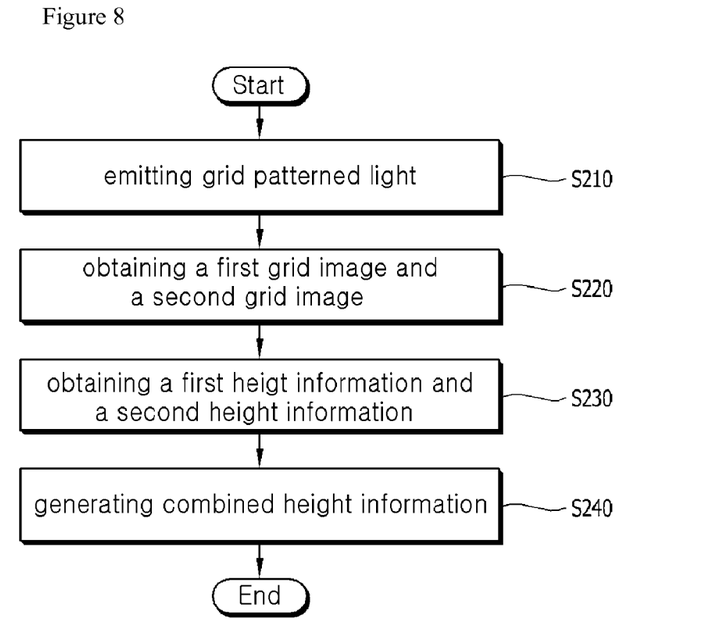
FIG. 8 is a flow chart showing a method of generating height information of a circuit board inspection apparatus according to another embodiment of the present invention.

FIG. 8 is a flow chart showing a method of generating height information of a circuit board inspection apparatus according to another embodiment of the present invention.

Referring to FIG. 8, in order to generate a height information in a circuit board inspection apparatus according to another exemplary embodiment, first, irradiating a measurement object formed on a board inspection apparatus with a grid patterned light (S210). Subsequently, obtaining a first grid patterned corresponding to the first area AR1 and a second grid patterned corresponding to the second area with partially overlapped to the first area AR1 of the measurement object 10 (S220). Subsequently, obtaining a first height information corresponding to the first grid patterned and a second height information corresponding to the second grid patterned using bucket algorithm for the obtained first and second grid images (S230). Consecutively, generating a combined height information by combining the first and second height information (S240). The obtained relative positioning relationship of the first and second areas by using the overlapped area of the first and second areas is used to combine the first and second grid images. Such a method may be applied generally to FIGS. 3-7 explained above, but it differs from combining height information after obtaining each of a first height information and a second height information.

The first height information may comprise a first measured height H1 and the second height information may comprise a second measured height H2.

Generating combined height information by combining the first and second height information using the relative positioning relationship (S240), wherein the obtained relative positioning relationship is obtained by using the overlapped area of the first and second areas, may be performed as below.

First, the first area and the second area are matched by using the positioning relationship, and a following equation is obtained in an overlapped area of the first and second areas.

$$H1 = aH2 + b$$ [Equation 2]

Herein, a is a scale factor, and b is a height difference. Also, H1 is a first height information and H2 is a second height information.

For example, the a and b may be obtained using least square method (LSM) with substitution of multiple H1 and H2.

A combined height information may be generated by using the obtained a and b after getting a and b which satisfies the equation 2.

Figure 9:
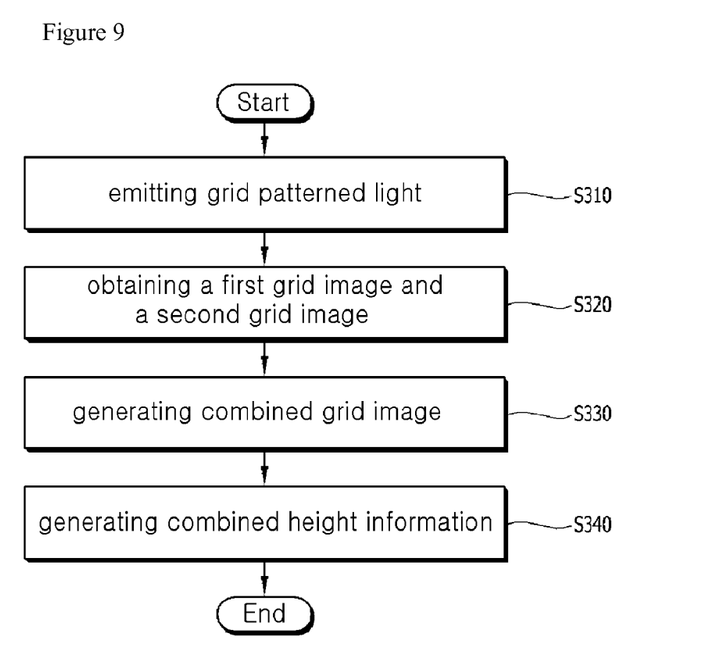
FIG. 9 is a flow chart showing another embodiment method of generating height information of a circuit board inspection apparatus.

FIG. 9 is a flow chart showing another embodiment method of generating height information of a circuit board inspection apparatus.

Referring to FIG. 9, in order to generate a height information in a circuit board inspection apparatus according to another exemplary embodiment, first, a grid patterned light is emitted (S310). Next, obtaining a first grid patterned corresponding to the first area AR1 and a second grid patterned corresponding to the second area with partially overlapped to the first area AR1 of the measurement object 10 (S320). The first and second grid images are obtained by capturing images of the first area and the second area with partially overlapped to the first area. Next, generating a combined grid image by combining the first and second grid images (S330). The obtained relative positioning relationship of the first and second areas by using the overlapped area of the first and second areas is used to combine the first and second grid images. Subsequently, obtaining a combined height information corresponding to the combined grid image using bucket algorithm (S340).

Such a method is similar to the method of FIG. 8 explained above, but it differs from generating the combined height information not after obtaining each of a height information form the first and second grid images but directly from the obtained grid image.

Generating combined grid image by combining the first and second grid images using relative positioning relationship between the first and second areas, wherein the positioning relationship is obtained by using overlapped area of the first and second areas, may be performed as below.

First, the first and second areas are matched by using the positioning relationship, and a following equation is obtained in an overlapped area of the first and second areas.

$$H1 = H2 + b$$ [Equation 3]

Herein, b is a height difference. Also H1 is a first height information and H2 is a second height information.

For example, the b can be obtained in a way of mean value, representative value, mode, etc., with substitution of multiple H1 and H2.

A combined grid image may be generated by using the obtained b, after getting b which satisfies the equation 3.

Meanwhile, a credibility index of the first and second grid images may be calculated and used. The credibility index may comprise at least one of single intensity, modulation, visibility and signal-to-noise of the grid patterned light. And one of inferior credibility, of the first region and the second region, may be compensated to the other of superior credibility According to the present invention above, a relative position relation between images obtained by a plurality of cameras is obtained and images are matched using the obtained position relation so that a precise matching image can be performed.

Thus, it is possible to obtain exact height information with high resolution and high inspection speed which are benefits of multiple camera usage by obtaining final height information from combined grid image or combined height information.

It will be apparent to those skilled in the art that various modifications and variation may be made in the present invention without departing from the spirit or scope of the invention. Thus, it is intended that the present invention cover the modifications and variations of this invention provided they come within the scope of the appended claims and their equivalents.

The invention claimed is:

1. A method of generating height information in a circuit board inspection apparatus comprising:
   capturing, by a camera, a first image corresponding to a first area of a test board and a second image corresponding to a second area of the test board which is partially overlapped with the first area;
   matching, by a central processor, the first image and the second image based on the overlapped area of the first area and the second area;
   obtaining, by the central processor, a relative positioning relationship between the first area and the second area by using the result of matching; and
   generating, by the central processor, a combined height information of a measurement object formed on a circuit board by combining a first grid image and a second grid image based on the relative positioning relationship, wherein the measurement object formed on the circuit board is irradiated, by a lighting source, with at least two grid patterned lights and the first grid image and the second grid image are captured by the camera.

2. The method of claim 1, wherein a plurality of dots are marked on the test board.

3. The method of claim 2, wherein an identifier is formed on the test board, and the identifier is formed within the overlapped area.

4. The method of claim 2, wherein matching the first image and the second image based on the overlapped area of the first area and the second area comprises:
   selecting feature dots among the plurality of dots within the overlap area; and
   matching feature dots of the first image and feature dots of the second image.

5. The method of claim 2,
   wherein the plurality of dots marked in the test board are aligned in a matrix,
   wherein the overlapped area comprises a matching line comprising at least one row of the matrix, and
   wherein the first image and the second image are matched based on the matching line.

6. The method of claim 5, before obtaining the first image corresponding to the first area of the test board and the second image corresponding to the second area of the test board which is partially overlapped with the first area further comprising:
   screening remaining dots of the matrix that are not included in the matching line such that the remaining dots of the matrix are not to be captured as the first image or the second image.

7. The method of claim 2, wherein matching the first image and the second image based on the overlapped area of the first area and the second area comprises:

generating a predicted image corresponding to the second area connected to the first image by using a shape of dot arrangement shown in the first image of the first area; and
matching the predicted image and the second image based on the overlapped area.

8. The method of claim 2, wherein obtaining the relative positioning relationship between the first area and the second area by using result of the matching comprises:
   obtaining numbers s, m11, m12, m13, m21, m22, m23, m31, m32, and m33 that satisfy an equation as expressed by;

$$s \begin{bmatrix} u1 \\ v1 \\ 1 \end{bmatrix} = \begin{bmatrix} m11 & m12 & m13 \\ m21 & m22 & m23 \\ m31 & m32 & m33 \end{bmatrix} \begin{bmatrix} u2 \\ v2 \\ 1 \end{bmatrix}$$

wherein (u1,v1) is a coordinate of the first area and (u2,v2) is a coordinate of the second area that are matched at one point within the overlapped area.

9. The method of claim 8, wherein matching the first image and the second image based on the overlapped area of the first area and the second area is characterized in matching at least five points to obtain the equation.

10. A method of generating height information in a circuit board inspection apparatus comprising:
    irradiating, by a lighting source, a measurement object formed on a circuit board inspection apparatus with at least two grid patterned lights;
    capturing, by a camera, a first grid image corresponding to a first area of the measurement object formed on the circuit board and a second grid image corresponding to a second area of the measurement object formed on the circuit board which is partially overlapped with the first area;
    obtaining, by a central processor, a first height information corresponding to the first grid image and a second height information corresponding to the second grid image by using bucket algorithm to the obtained first and second grid images; and
    generating, by the central processor, a combined height information of the measurement object formed on the circuit board by combining the first height information and the second height information using a relative positioning relationship between the first area and the second area, wherein the relative positioning relationship is obtained, by the central processor, by using an overlapped area of a first area and a second area of a test board.

11. The method of claim 10, wherein the first height information comprises a first measured height H1 and the second height information comprises a second measured height H2, and wherein generating the combined height information by combining the first height information and the second height information using the relative positioning relationship between the first area and the second area comprises:
    matching the first area and the second area by using the relative positioning relationship;
    obtaining a and b that satisfy an equation H1=aH2+b within the overlapped area of the first area and the second area, wherein a is a scale factor and b is a height difference; and
    generating the combined height information by using the obtained a and b.

12. A method of generating height information in a circuit board inspection apparatus comprising:
  irradiating, by a lighting source, a measurement object formed on a circuit board inspection apparatus with at least two grid patterned lights;
  capturing, by a camera, a first grid image corresponding to a first area of the measurement object formed on the circuit board and a second grid image corresponding to a second area of the measurement object formed on the circuit board which is partially overlapped with the first area;
  generating, by a central processor, a combined grid image by combining the first grid image and the second grid image using a relative positioning relationship between the first area and the second area, wherein the relative positioning relationship is obtained, by the central processor, by using an overlapped area of a first area and a second area of a test board; and
  obtaining, by the central processor, a combined height information by combining a first height information H1 corresponding to the first grid image and a second height information H2 corresponding to the second grid image using a bucket algorithm to the combined grid image.

13. The method of claim 12, wherein generating the combined grid image by combining the first grid image and the second grid image using the relative positioning relationship between the first area and the second area, wherein the relative positioning relationship is obtained by using the overlapped area of the first area and the second area, comprises:
  matching the first area and the second area using the relative positioning relationship;
  obtaining b that satisfies an equation H1=H2+b within the overlapped area of the first area and the second area, wherein b is a height difference; and
  generating the combined grid image using the obtained b.

14. The method of claim 10 further comprising:
  calculating a credibility index of the first grid image and the second grid image, wherein the credibility index comprises at least one of received signal intensity, modulation, visibility, and signal-to-noise ratio of the grid patterned light and one of inferior credibility, of the first region and the second region, is compensated to the other of superior credibility.

15. The method of claim 12 further comprising:
  calculating a credibility index of the first grid image and the second grid image, wherein the credibility index comprises at least one of received signal intensity, modulation, visibility, and signal-to-noise ratio of the grid patterned light and one of inferior credibility, of the first region and the second region, is compensated to the other of superior credibility.

* * * * *